(12) United States Patent
Miller

(10) Patent No.: US 6,582,371 B2
(45) Date of Patent: Jun. 24, 2003

(54) ULTRASOUND PROBE WIRING METHOD AND APPARATUS

(75) Inventor: David G. Miller, North Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/919,238

(22) Filed: Jul. 31, 2001

(65) Prior Publication Data

US 2003/0028105 A1 Feb. 6, 2003

(51) Int. Cl.[7] ............................................. A61B 8/14
(52) U.S. Cl. ...................... 600/459; 361/784; 29/25.35; 29/854
(58) Field of Search ........................ 600/407–471; 73/625, 626; 29/25.35, 854; 367/153, 173; 439/59–85, 620–629; 174/250, 255–261; 310/322, 325, 330–334, 337, 366; 361/784, 796–802

(56) References Cited

U.S. PATENT DOCUMENTS

| | | | |
|---|---|---|---|
| 5,398,689 A | * 3/1995 | Connor et al. | 600/459 |
| 5,669,389 A | 9/1997 | Rotteveel et al. | 128/662.06 |
| 5,795,299 A | * 8/1998 | Eaton et al. | 600/459 |
| 5,947,905 A | * 9/1999 | Hadjicostis et al. | 600/463 |
| 6,049,958 A | 4/2000 | Eberle et al. | 29/25.35 |
| 6,142,930 A | 11/2000 | Ito et al. | 600/109 |

FOREIGN PATENT DOCUMENTS

EP 0671221 A2 9/1995

\* cited by examiner

Primary Examiner—Marvin M. Lateef
Assistant Examiner—Ali M. Imam
(74) Attorney, Agent, or Firm—John Vodopia

(57) ABSTRACT

Wiring an IC, using flexible circuits, by relating a circuit board to an IC and using traces on the circuit board as a second set of input to the IC. More specifically, a set of first lands on the circuit board are connected to a first set of lands on the IC. The circuit board and IC are positioned so as to present a second set of lands on the circuit board in close proximity to a second set of lands on the IC. A first flex circuit is connected to the second lands on the circuit board while a second flex circuit is connected to the second lands on the IC. The flex circuits may be connected to signal wires or may serve themselves as the main signal wires.

7 Claims, 9 Drawing Sheets

ULTRASOUND PROBE WIRING METHOD AND APPARATUS

BACKGROUND OF THE INVENTION

The present invention relates to apparatus and methods for connecting electrical leads (wires, traces, etc. . . . ) to a device and in particular to apparatus and methods for connecting a large number of leads to a device contained in a relatively small area, such as an IC chip in a housing for a transesophageal ultrasound probe.

Non-invasive, semi-invasive and invasive ultrasound probes have been widely used to view tissue structures, such as the heart, the abdominal organs, the fetus, and the vascular system. Semi-invasive systems include transesophageal imaging systems, while invasive systems include intravascular imaging systems. Depending on the type and location of the tissue, different systems provide better access to or improved field of view of internal biological tissue.

An ultrasound probe usually comprises at least one transducer element, typically formed of PZT material, and may comprise a one or two dimensional array of such elements. In general, each element must be connected to a separate lead and a common ground plane. Since many of the proposed two dimensional arrays have a significant number of elements (for example even a relatively small 56×56 array has 3,136 elements) the number of required connections is quite large. Forming connections between the drive circuits and such an array of elements has proven challenging.

One of the more specialized types of ultrasound probes is the transesophageal probe (TEE Probe) which is formed on a long slender body placing sever limitations on the mechanical and electrical design thereof. Specifically, TEE probes have considerable space constraints that must be observed when designing the probe. This affects not only the size of the elements (and therefore the array), but also the volume available to connect the leads to the array. While known one-dimensional arrays typically have a fine horizontal pitch with a coarse vertical pitch, many proposed two dimensional arrays are finely pitched in both directions having horizontal and vertical measurements of less than 5 mm. In a non-invasive probe, adequate room for such connection may be created, but in an invasive probe, such as a TEE probe, space is severely limited and every square nanometer is valuable. It has been extremely difficult to design a TEE probe which provides a significant number of discrete leads within the space allowed by the overall design of the probe and more importantly it has proven difficult to connect any significant number (such as are required for a 2-D transducer assembly) of leads to their respective elements in the array. Traditional connections either require too much space or are too difficult to implement as part of an assembly process.

The present inventor has invented a method and apparatus permitting the connection of a large number of leads to a device wherein such connections must be implemented in a relatively small area. Such methods and apparatus are well adapted for use with TEE probes and other ultrasound probes.

BRIEF DESCRIPTION OF THE DRAWINGS

An understanding of the present invention can be gained from the following detailed description of the invention, taken in conjunction with the accompanying drawings of which.

DETAILED DESCRIPTION OF THE INVENTION

Figure 1:
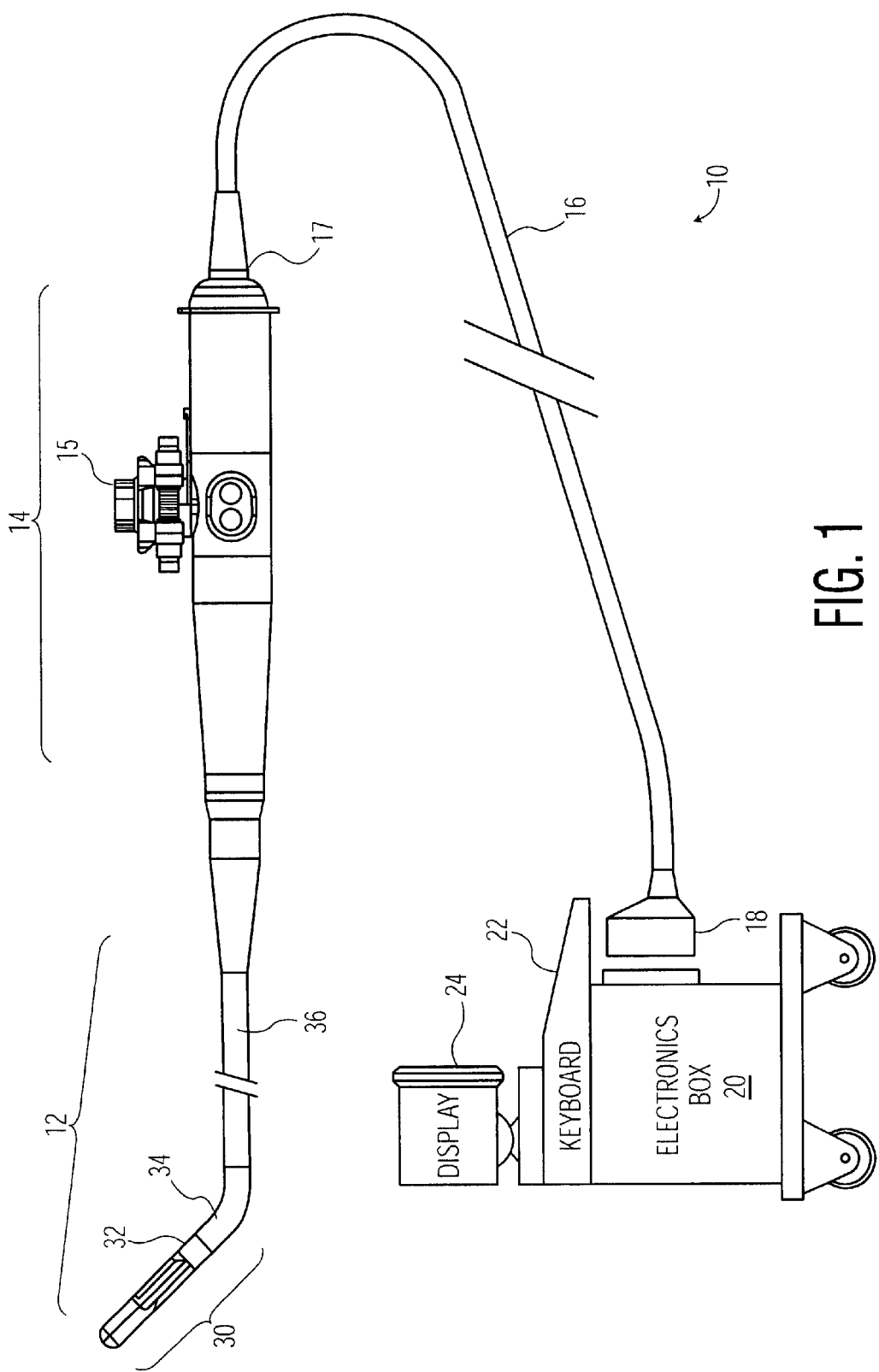
FIG. 1 is an illustration of an ultrasound system including a transesophageal imaging probe.

Reference will now be made in detail to the present invention, an example of which is illustrated in the accompanying drawings, wherein like reference numerals refer to like elements throughout.

While the apparatus set forth in the present application is described as being specifically constructed for ultrasound imaging, the methods and apparatus recited herein may be used to solve a variety of similar problems (a large number of connection in a limited volume) in other fields. The methods and apparatus presented herein are not inherently related to any particular ultrasonic system, computer or other apparatus. Devices which may benefit from the present invention include those manufactured AGILENT TECHNOLOGIES.

FIG. 1 is an illustration of an ultrasound system 10 including a transesophageal imaging probe 12. The ultrasound imaging system 10 includes the transesophageal probe 12 (referred to herein as a "TEE probe") with a probe handle 14, connected by a cable 16, a strain relief 17, and a connector 18 to an electronics box 20. Electronics box 20 is interfaced with a keyboard 22 and a video display 24. The electronics box 20 generally includes a transmit beamformer, a receive beamformer, and an image generator. TEE probe 12 has a distal part 30 connected to an elongated semi-flexible body 36. The proximal end of elongated part 36 is connected to the distal end of probe handle 14. Distal part 30 of probe 12 includes a rigid region 32 and a flexible region 34, which is connected to the distal end of elongated body 36. Probe handle 14 includes a positioning control 15 for articulating flexible region 34 and thus orienting rigid region 32 relative to tissue of interest. Elongated semi-flexible body 36 is constructed and arranged for insertion into the esophagus. The entire TEE probe 12 is about 110 cm long and is about 9 mm in diameter.

Figure 2:
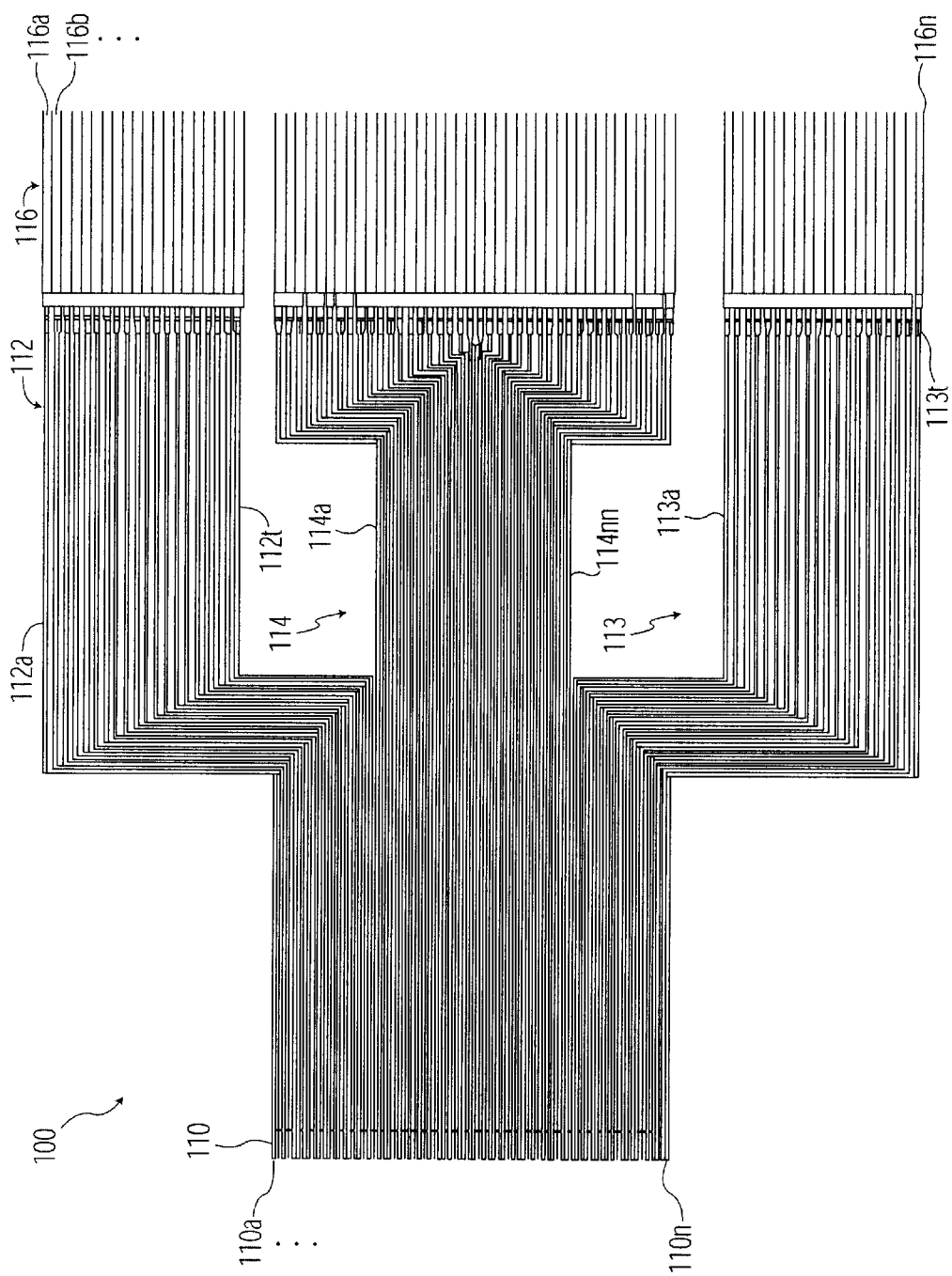
FIG. 2 is a plan view of a flexible circuit in accordance with a preferred embodiment of the present invention.
Figure 3:
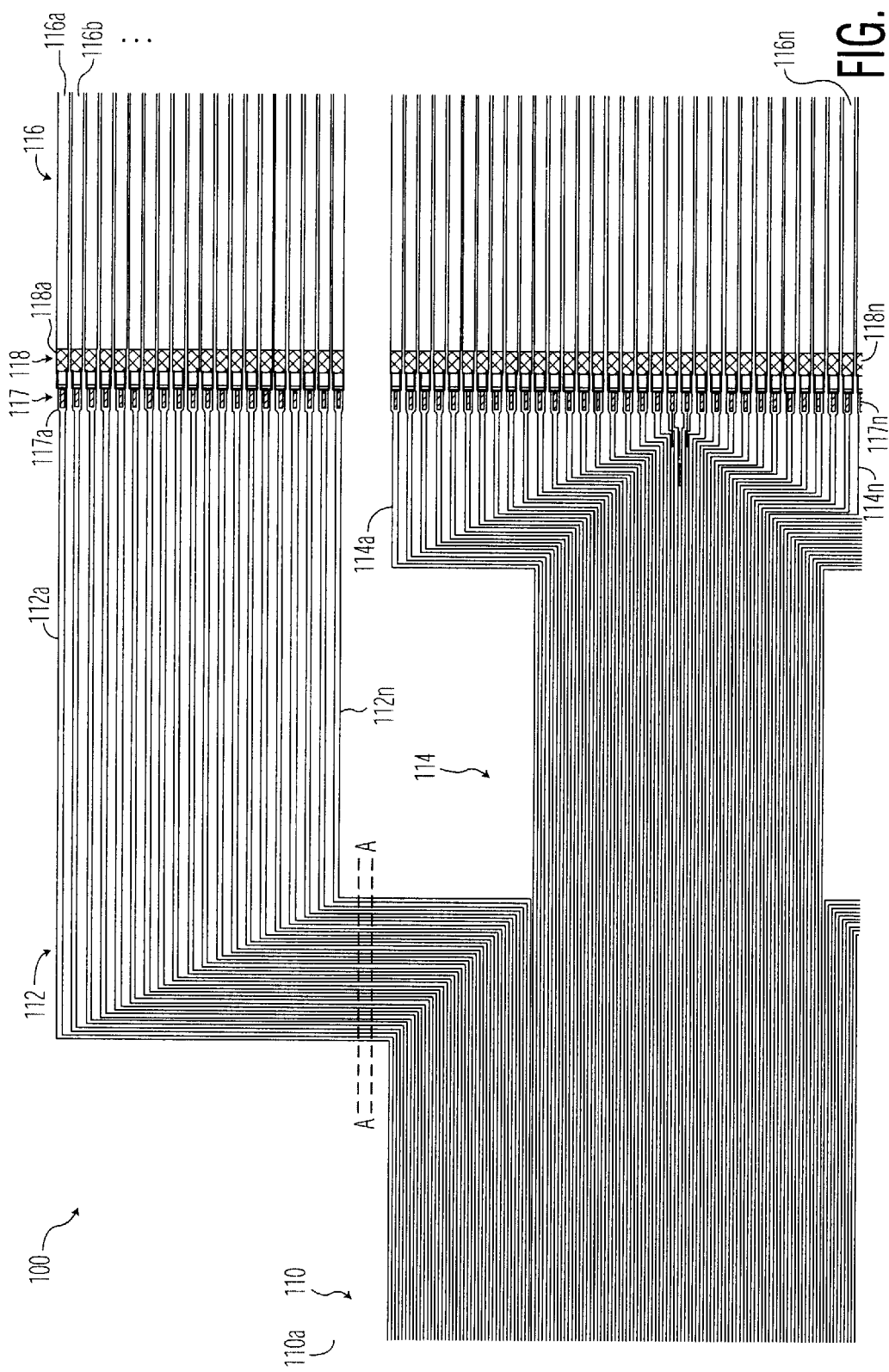
FIG. 3 is an enlarged partial view of the flexible circuit shown in FIG. 2.
Figure 4:
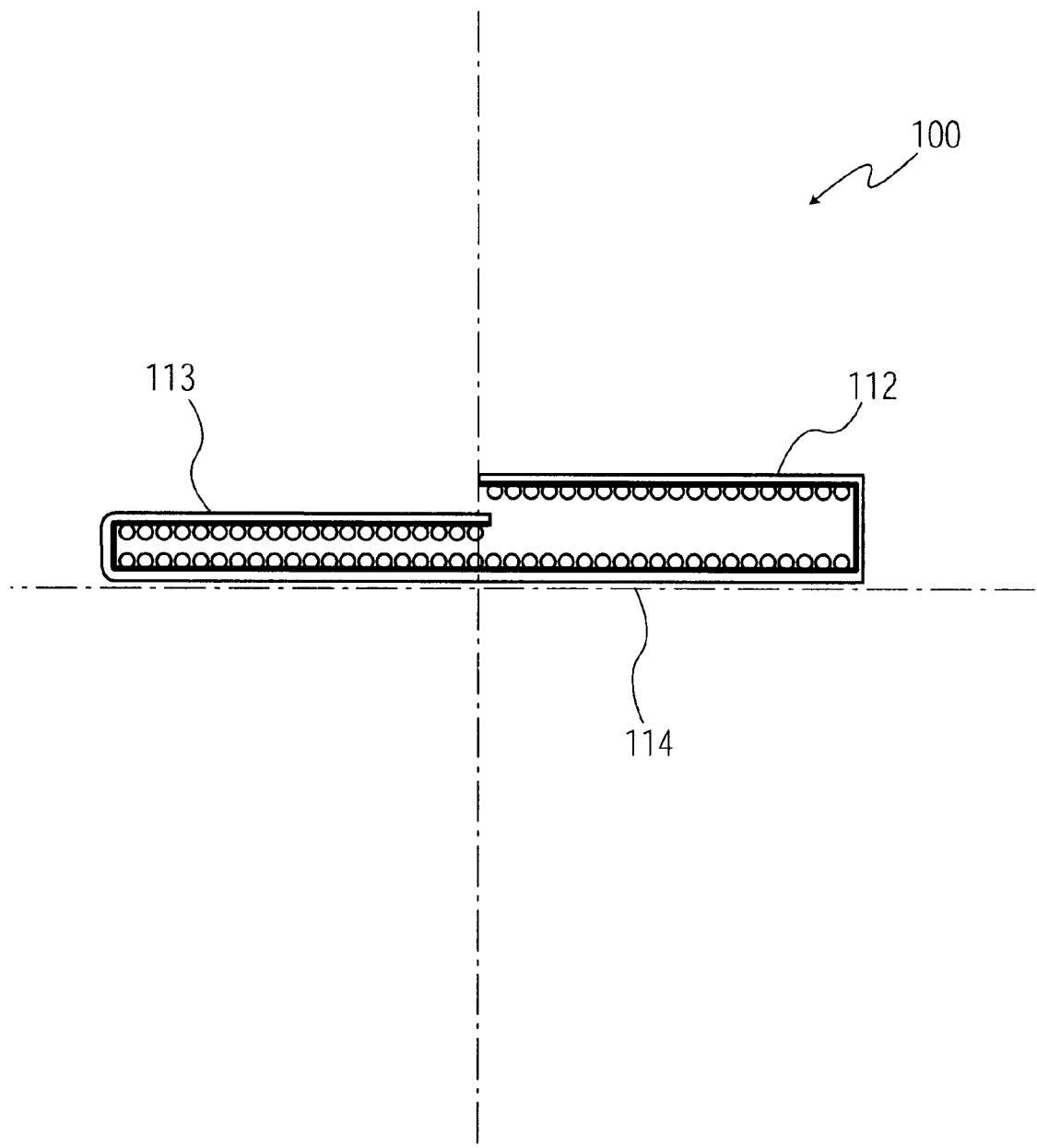
FIG. 4 is a cross-sectional view of the flexible circuit of FIG. 2.

FIGS. 2 through 4 show a flexible circuit 100 (also referred to herein as a "flex circuit 100") in accordance with the preferred embodiment of the present invention. FIG. 2 is a plan view of the flex circuit 100 in accordance with a preferred embodiment of the present invention, and more specifically shows the flex circuit 100 in an "unfolded" position. The flex circuit 100 serves to connect leads, typically small diameter co-axial cables, from the elongated semi-flexible body 36 (see FIG. 1) to transducer elements and may, for example, be constructed in accordance with the teachings of U.S. Pat. No. 5,296,651, owned by the assignee of the present invention and incorporated herein by reference. In accordance with such teaching, the flex circuit 100 may, but not necessarily, be provided with a ground plane (not shown).

The flex circuit 100 has a first end 110 comprised of leads 110a–110n for electrical connection to a structure such as an IC chip. In general, an element reference with just a number refers to a unitary whole or a collection of elements, while an element reference with a number and a letter refers to individual elements of the collection (typically an individual leads). The leads 110a–110n on the first end 110 are preferably spaced to have a pitch of 110 micrometers. This density permits the use of tape-automated bonding (TAB), preferably utilizing thermosonic welding, to physically construct the required connections. To facilitate TAB bonding, the leads 110a–110n of the flex circuit 100 may be formed so as to overhang or cantilever.

Opposite the first end 110, the leads in the flex circuit 100 are divided into three branches, a first outer branches 112 a second outer branch 113 and a center branch 114. The example shown in FIG. 2 has: 20 signal lines 112a–112t in the outer branch 112; 20 signal lines 113a–113t in outer branch 113; and 40 signal lines 114a–114nn in the center branch 114. The number of lines was selected more for symmetry and ease of explanation and can easily be varied based on need and/or design limitations. The leads in each of the branches 112, 113, and 114 are spread apart to facilitate connection to a plurality of small diameter co-axial cables 116a through 116n (for ease of explanation the description that follows herein will typically refer to the plurality of co-axial cables as cables 116). As shown in FIG. 2, the increase in pitch of the individual traces is accomplished using two 90° bends. The leads in the three branches 112, 113, and 114 preferably have a pitch of 200 micrometers facilitating connection to the co-axial cables 116.

In this manner, a single flex circuit 100 can provide connections to at least 80 cables 116 as shown in FIG. 2. Additionally, in accordance with the teachings of the '651 patent discussed herein above, the flex circuit 100 may be provided with a ground plane. Those of ordinary skill in the art will recognize that the exact configuration of the flex circuit 100, including the number of leads and the presence of a ground plane, may be modified to suit a variety of factors, including cost, number of signal channels, required flexibility, etc. . . .

FIG. 3 is an enlarged partial view of the flexible circuit 100 shown in FIG. 2. FIG. 3 illustrates some of the detail of the connections between the co-axial cables 116 and the flex circuit 100. Each of the coaxial cables 116a–116n are preferably stripped, tinned, and soldered to the flex circuit 100. Each of the coaxial cables 116 are soldered at two locations: an exposed inner conductor 117; and an exposed outer conductor 118. Each of the inner connectors 117 are soldered to a separate lead of the flexible circuit 100, for example lead 116a. Each of the outer conductors 118 may be soldered to a ground plane (not shown) of the flex circuit 100. Of course, if the flex circuit 100 does not include a ground plane, each of the outer connectors 118 may be electrically tied together and connected to an external ground plane, such as a copper foil, using any of a variety of methods known to those of ordinary skill in the art. Alternatively, each of the outer connectors 118 can be used as a signal path with other arrangements being made for ground (such as a dedicated signal path).

FIG. 4 is a cross-sectional view of the flex circuit 100 in a folded position. To facilitate use in a small volume, the outer branches 112 and 113 are folded over the center branch 114, as shown in FIG. 4. Referring to FIG. 3, a sample fold line A—A is shown for the outer branch 112. This maintains the appropriate density of leads while facilitating assembly. In the configuration shown in FIG. 4, the branch 112 is folded lower than the branch 113 with only a minimal overlap, however those of ordinary skill in the art will recognize the endless possibilities, for example folding the outer branched completely over one another or even rolling the outer branches 112 and 113. During assembly, the connections between the leads of the flex circuit 100 and the cables 116 can be made while the flex circuit 100 is unfolded. After formation of all of the appropriate connections the flex circuit 100 can be folded, rolled or whatever, prior to final assembly.

Figure 5:
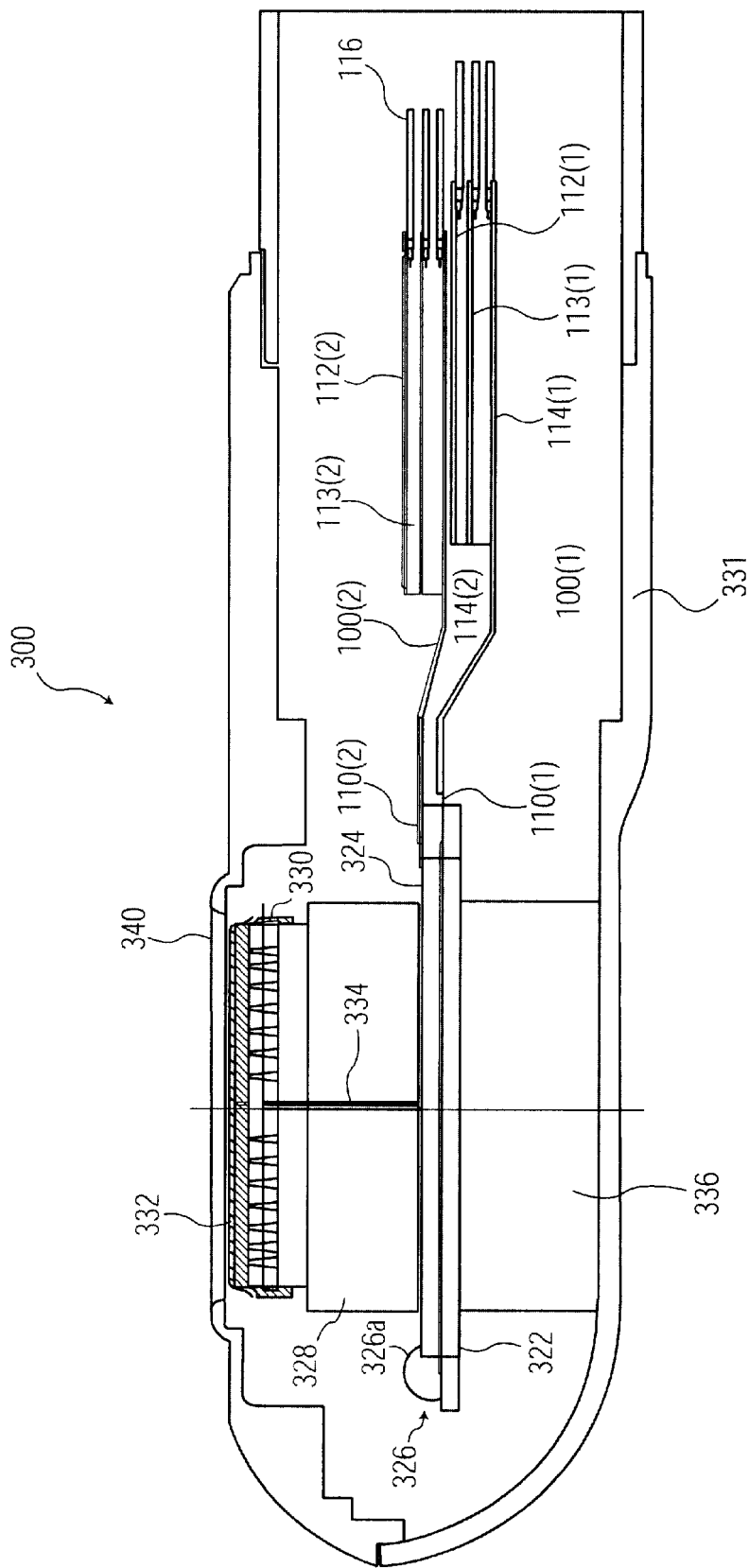
FIG. 5 is a cross-sectional view of a transesophageal imaging probe in accordance with the preferred embodiment of the present invention.

FIG. 5 is a cross-sectional view of a transesophageal probe 300 in accordance with the preferred embodiment of the present invention. The TEE probe 300 uses two of the flexible circuits 100 shown in FIG. 2. Those of ordinary skill in the art will recognize that the number of flexible circuits 100 required for any given probe is variable, two was selected for this example to illustrate the use of multiple flexible circuits 100. The two flexible circuits are labeled 100a and 100b. The Transesophageal (TEE) probe 300 is formed by a housing 331 with an attached lens 340 through which imaging is performed. The housing 331 securely holds a transducer assembly behind the lens 340. As with prior transesophageal imaging probes, the probe 300 is connected to an elongated semi-flexible body is, in turn, connected to a probe handle (also not shown, but may be as described with respect to FIG. 1).

The transducer assembly includes a circuit board 322, having a first and second set of lands, affixed to an IC 324, also having a first and second set of lands. The IC 324 distributes the signals carried by the cables 116 to the matrix of transducer elements 332, located inside the housing 331. Due to space constraints, the attainable pitch of connections to the IC 324 and the number of required connections, connections (lands) are spread over two edges of the IC 324. In accordance with the preferred embodiment of the present invention, the circuit board 322 acts as a pass through, interfacing a portion of the cables 116 with lands on the IC 324. As shown in FIG. 5, the first end 110(1) of the first flex circuit 100(1) is connected to a first set of lands on a first edge of the circuit board 322, using for example TAB bonding, while the first end 110(2) of the second flex circuit 100(2) is connected to the first set of lands on the IC 324, using for example TAB bonding. The circuit board 322 provides a set of traces that connect a first set of lands on one edge of the circuit board 322 to second set of lands on a second edge of the circuit board 322. The second set of lands on the circuit board 322 are connected to a second set of lands on a second edge of the IC 324.

The IC 324 is preferably acoustically matched to the circuit board 322 and bonded thereto using a thin epoxy bond. The use of the circuit board 322 provides a transducer assembly with improved thermal conductivity and better acoustic properties than simply running the cable 100(1) directly to the second set of lands on the IC 324.

In the structure illustrated in FIG. 5, the circuit board 322 extends past the IC 324, on at least one edge thereof, to provide two different input surfaces separated vertically and laterally. Preferably, the circuit board 322 and the IC 324 are related to each other so as to provide access for the cables 116 to two sets of lands, the first set on the circuit board 322 and the first set on the IC 324. Preferably, the circuit board 322 has a lateral area (lateral being the direction along the extend of the probe 300) greater than the IC 324. However, those of ordinary skill in the art will recognize that this need not be the case, in fact the circuit board 322 and the IC 324 could have the same lateral area (with a staggered relationship) or the IC 324 could have the greater lateral area.

As noted, the IC 324 is provided with at least two set of lands, preferably on at least two edges thereof, and more preferably at opposite ends thereof. The first set of lands has a pitch equivalent to the pitch of leads 110(2)$a$–110(2)$n$ on the first end 110(2) of the flex circuit 100(2) and is positioned within the probe 300 to facilitate connection thereto. Similarly, the circuit board 322 is provided with at least two set of lands, preferably on at least two edges thereof, and more preferably on opposite ends thereof. The first set of lands has a pitch equivalent to the density of leads 110(1)$a$–110(1)$n$ on the first end 110(1) of the flex circuit 100(1) and is positioned within the probe 300 to facilitate connection thereto. The pitch on the second set of lands on the IC 324 and the circuit board 322 are dictated by the technology used to form the connection.

For example, the IC 324 and the circuit board 322 may be electrically connected by a plurality of wires 326 (only one of which, 326$a$, can be seen in FIG. 5) extending between the second set of lands on the IC 324 and the second set of lands on the circuit board 322. TAB bonding, which supports a pitch of 100 micrometers, is one preferred way to form this of connection.

Those of ordinary skill in the art will appreciate that the circuit board 322 may be replaced with multiple circuit boards depending on the required number of leads. Each additional circuit board could protrude a little further out on both lateral ends to provide the necessary land space for the formation of connections.

The circuit board 322 and the IC 324 are part of a transducer assembly which can be thought of as a stack of layers, sometimes referred to as a transducer stack. A first block 328, preferably made of heat dissipating material, may be situated above the IC 324, while a second block 336, also preferably made of heat dissipating material, may be situated below the circuit board 322. The materials forming the blocks 328 and 336 are also selected based on desired acoustic properties as is known to those of ordinary skill in the art. For example, it is often desirable to absorb vibrations, which would lead one of ordinary skill in the art to form the blocks 328 and 336 of acoustically absorptive material.

The connection between the IC 324 and the matrix of transducer elements is beyond the scope of the present invention. Details of such connections can be found in co-pending U.S. patent application Ser. No. 09/919,470, entitled System for Attaching an Acoustic Element to an Integrated Circuit, assigned to the assignee of the present application and incorporated herein by reference. An alternative methodology for such a connection can be found in U.S. Pat. No. 5,267,221. Accordingly, only the briefest of explanations is presented herein.

A connection 334 provides electrical connectivity to the matrix of transducer elements 332, using, for example, a plurality of leads. A redistribution system 330 connects the leads of the connection 334 to the individual elements of the matrix of transducer elements 332. The redistribution layer may also be constructed so as to provide support and provide some acoustic isolation for the matrix of transducer elements 332 and may act as a layer of backing material. The physical structure of the connection 334, and in particular the redistribution system, may be any of a variety of known structures for connecting an IC to a matrix of transducer elements. Co-pending U.S. patent application Ser. No. 09/919,470, assigned to the assignee of the present application, entitled System for Attaching an Acoustic Element to an Integrated Circuit describes a method and apparatus for forming such a connection, including the use of a re-distribution layer to match the pitch of the IC 324 with the pitch of the matrix of transducer elements 332. As shown in the co-pending application, the circuit board 322 and IC 324 can be placed next to the matrix of transducer elements 332 rather than being separated by the block 328. The order and placement of the various components in the transducer stack may vary based on design and product goals. Currently, one of the most important goals of the transducer design is thermal management. Accordingly, the configuration shown in the co-pending application may in fact provide superior thermal connectivity and management. In the present application, the circuit board 322 and IC 324 are shown separated from the IC 324 simply for ease of explanation.

The structure shown in FIG. 5 permits the connection of a large number (>100) of leads to the matrix of elements 130 in a relatively constrained area by using the circuit board 322 to provide, in effect, another set of lands in close proximity to the first set of lands on the IC 324. An additional benefit of the configuration disclosed in FIG. 5 is modularization providing for more efficient assembly of the TEE probe as a whole. The illustrated configuration also promotes efficient heat dissipation and sound absorption.

Figure 6:
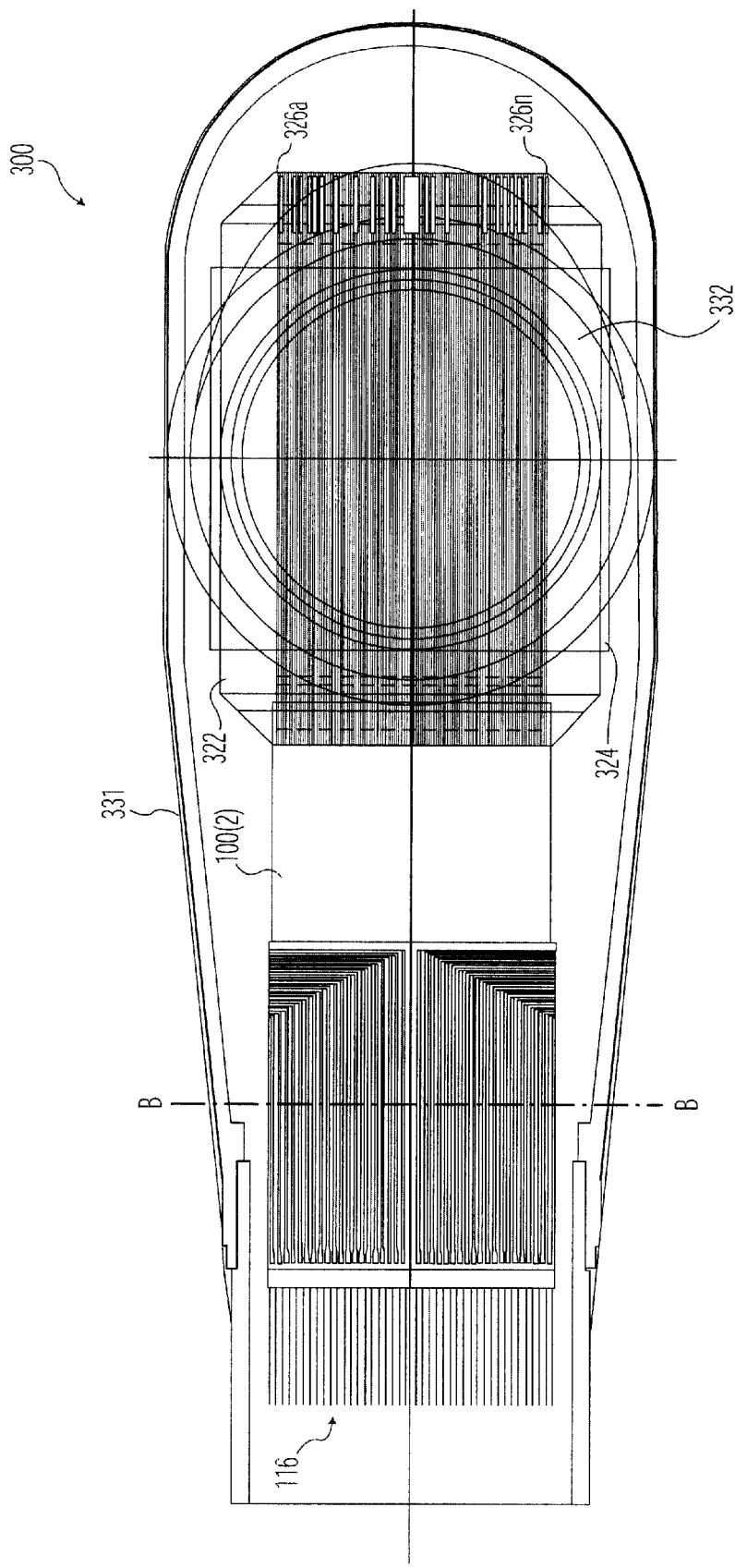
FIG. 6 is a top down cross-sectional view of the transesophageal imaging probe shown in FIG. 5 in accordance with the preferred embodiment of the present invention.
Figure 7:
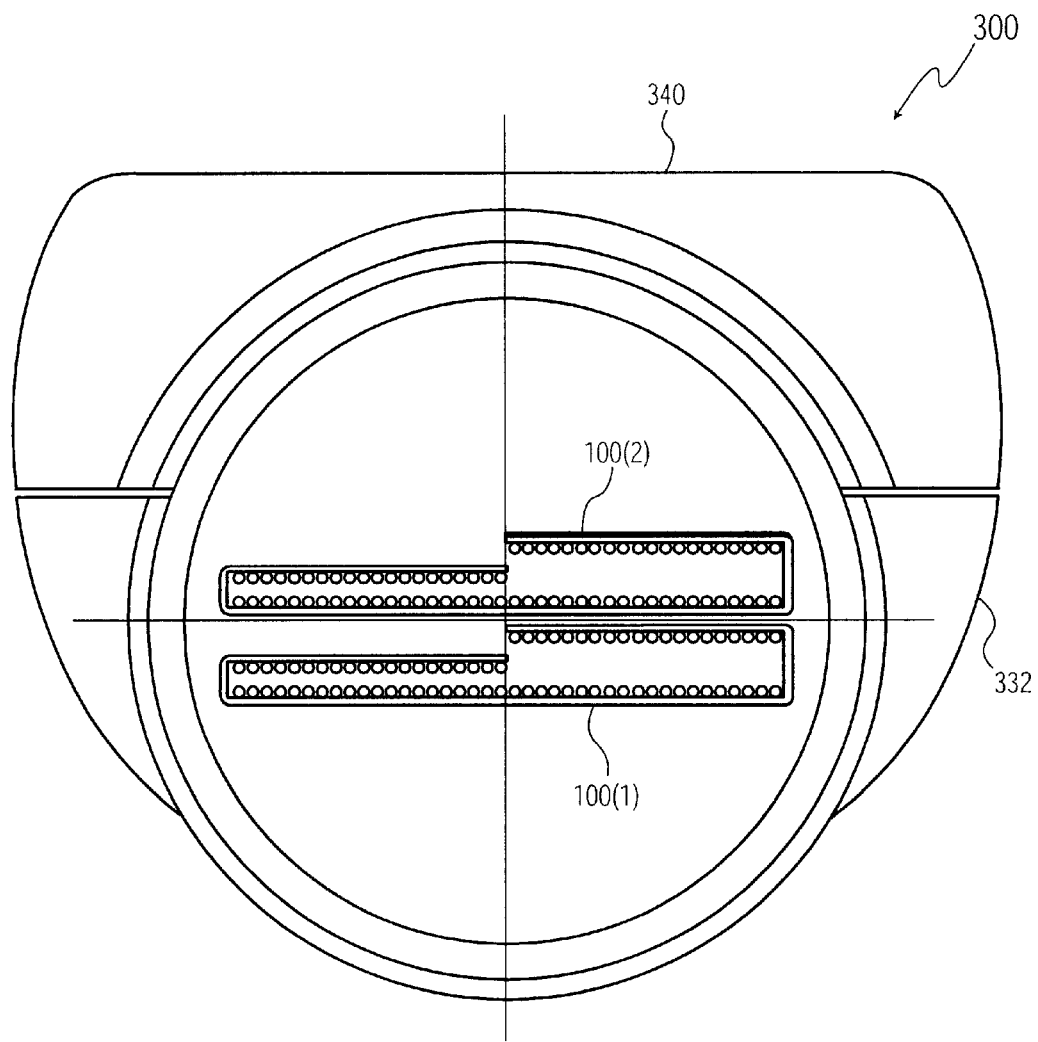
FIG. 7 is a cross-sectional view of the transesophageal imaging probe shown in FIG. 5 taken along line B—B shown in FIG. 6.

FIGS. 6 and 7 show alternative views of the TEE probe 300. FIG. 6 is a top down cross-sectional view of the TEE probe 300 shown in FIG. 5 in accordance with the preferred embodiment of the present invention. FIG. 7 is a cross-sectional view of the TEE probe 300 of FIG. 5 taken along line B—B shown in FIG. 6.

Figure 8:
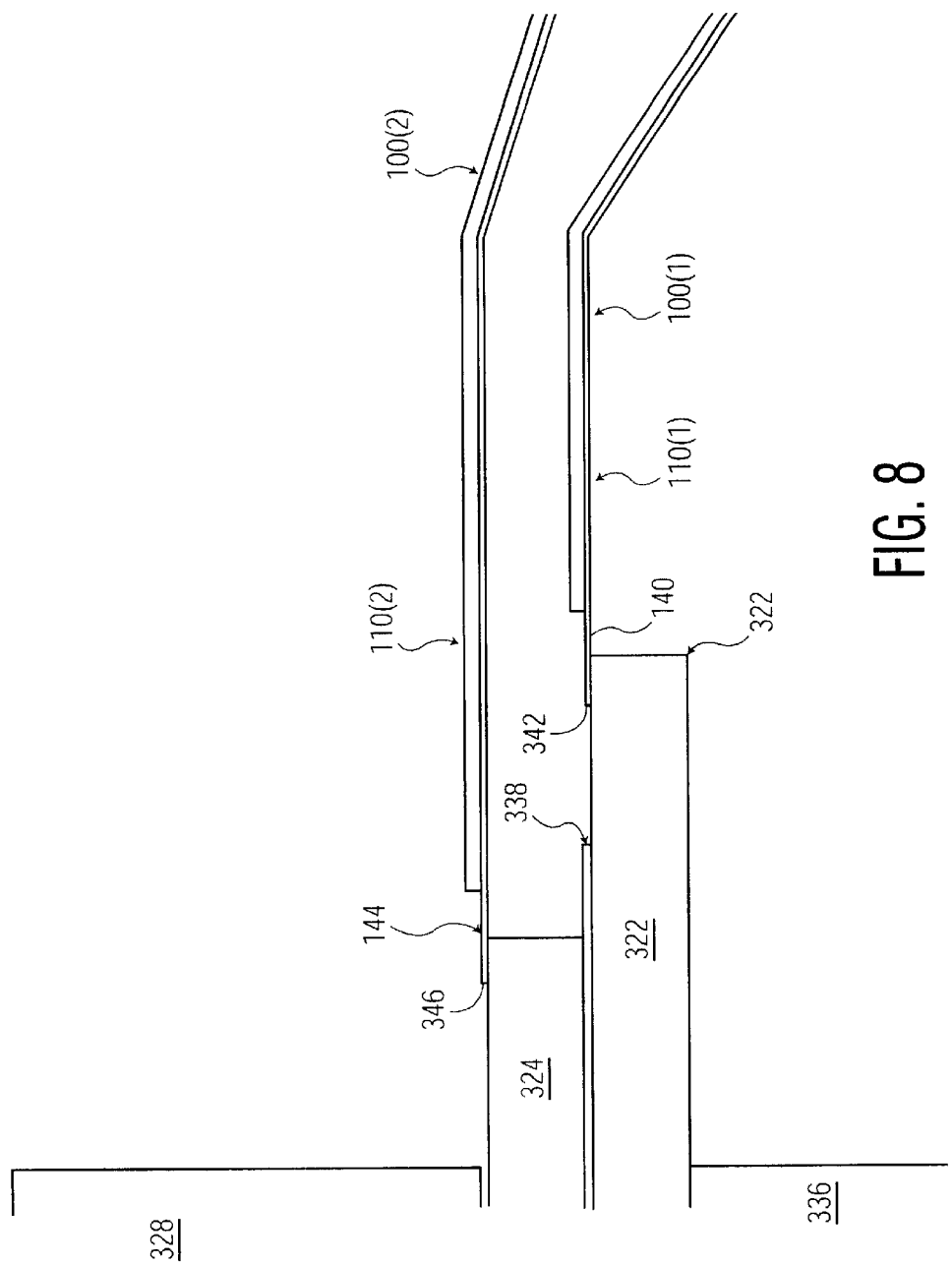
FIG. 8 is a diagram of connections between the flexible circuit shown in FIG. 2 and the circuit board and the IC shown in FIG. 5.

FIG. 8 is a diagram of connections between the flexible circuits 100(1) and 100(2) shown in FIG. 5 and the circuit board 322 and IC 324 also shown in FIG. 5. The circuit board 322 is supported by the block 336 and connected to the IC 324 via a thin epoxy bond 338 which extends past the area of interface, but not so far as to interfere with the connection of the flex circuit 100(1) with the circuit board 322. As noted, the first end 110(1) of the flex circuit 100(1) is provided with overhanging or cantilevered leads 140 so as to permit the formation of a TAB bond with lands 342 on the circuit board 322. Similarly, the end 110(2) of the flex circuit 100(2) is provided with overhanging or cantilevered leads 144 so as to permit the formation of a TAB bond with lands 346 on the IC 324. If the flex circuit 100(2) contains a ground plane, the ground plane can be connected to the IC 324 using a variety of means, including the use of a additional wire or by dedicating a wire within the flex circuit 100(2) to the ground plane. Similar arrangements can be made with the flex circuit 100(1) to provide a ground plane therefor.

Figure 9:
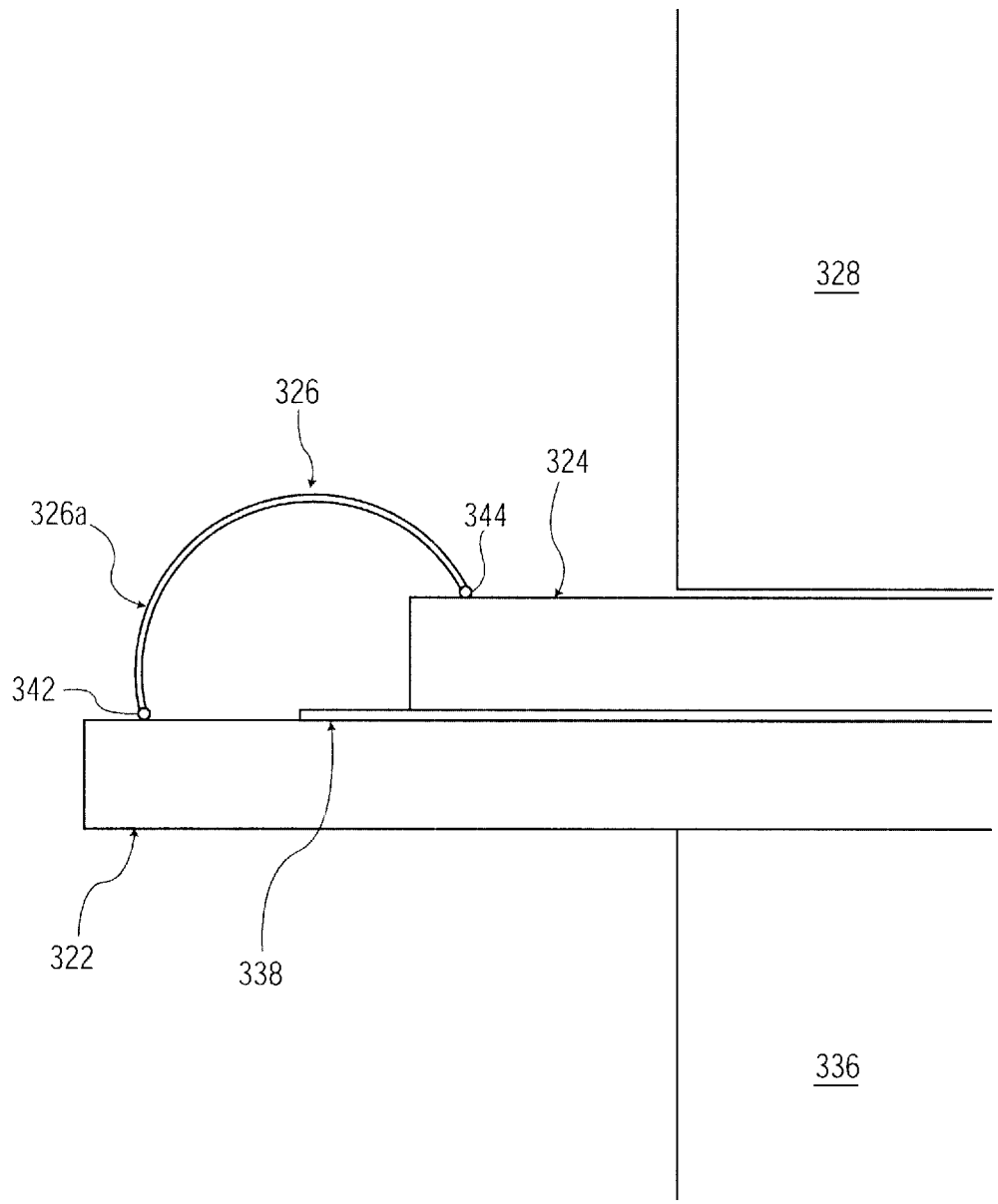
FIG. 9 is a diagram of connections between the circuit board shown in FIG. 5 and the IC also shown in FIG. 5.

FIG. 9 is a diagram of connections between the circuit board 322 shown in FIGS. 5 and 5. the IC 324 also shown in FIG. 5. For each lead to be connected to the IC 324 a wire 326$n$ is bonded (for example using a wire bond, an ultrasonic bond, a thermosonic bond or a ball bond) to a land 342$n$ on the circuit board 322 and the corresponding land 344$n$ on the IC 324. While FIG. 9 only shows a single wire 326$a$, those of ordinary skill in the art will recognize that a plurality of wires would be used, preferably at least one per lead on the flex circuit 100(1), e.g., 80. Those of ordinary skill in the art will recognize equivalent structures for the wires 326, including for example flex circuits or ribbon cables. Further, if the flex circuit is provided with a ground plan, as discussed herein above, an additional trace on the bottom of the circuit board 322 can be provided to bring the signal path to the opposite end thereof Such a ground trace can be brought to the top of the circuit board 322, for connection to the IC 324, in a variety of known manners, including an extra wire, a pass through, etc. . . .

Although a preferred embodiment of the present invention has been shown and described, it will be appreciated by those skilled in the art that changes may be made in such embodiment without departing from the principles and spirit of the invention, the scope of which is defined in the claims and their equivalents.

What is claimed is:

1. An ultrasound probe comprising:
    a plurality of transducer elements; an IC having a first and second set of lands on two different areas thereof, the IC being connected to the plurality of transducer elements via a communication channel there between;
    a circuit board bonded to the IC, the circuit board having a first and second set of lands on two different areas thereof, the first set of lands being electrically connected to the second set of lands, wherein the first set of lands is in close proximity to the first set of lands on the IC and the second set of lands being connected to the second set of lands on the IC;
    a first flex circuit connected to the first lands of the circuit board so that electrical leads on the flex circuit are in communication with the second set of lands on the IC; and
    a second flex circuit connected to the first set of lands on the IC.

2. The ultrasound probe, as set forth in claim 1, wherein the plurality of transducer elements comprises a two-dimensional array of elements.

3. The ultrasound probe, as set forth in claim 2, wherein the first flex circuit comprises:
    a first end, having leads with a first density, connected to the first lands of the circuit board; and
    a second end divided into branches, wherein in each of the branches has leads with a density less than the first density.

4. The ultrasound probe, as set forth in claim 3, wherein the second end of the first flex circuit is divided into a first outer branch, a second outer branch, and a center branch, and wherein the first outer branch and the second outer branch are folded over the center branch.

5. The ultrasound probe, as set forth in claim 3, wherein the leads of the second end of the first flex circuit are connected to wires.

6. The ultrasound probe, as set forth in claim 3, wherein the leads of the second end of the first flex circuit are soldered to wires.

7. The ultrasound probe, as set forth in claim 1, wherein the first flex circuit is TAB bonded to the first lands of the circuit board.

* * * * *